United States Patent [19]

Ryan et al.

[11] 4,444,576
[45] Apr. 24, 1984

[54] ENERGY-SAVING DISTILLATIVE SEPARATION USING LOW-TEMPERATURE HEAT INPUT

[75] Inventors: James M. Ryan, Weston; John V. O'Brien, Shrewsbury, both of Mass.

[73] Assignee: Koch Process Systems, Inc., Westboro, Mass.

[21] Appl. No.: 438,179

[22] Filed: Nov. 1, 1982

[51] Int. Cl.³ .............................................. B01D 3/40
[52] U.S. Cl. ......................................... 62/20; 62/28; 203/24; 203/26; 203/DIG. 4
[58] Field of Search ...................... 203/24, 26, DIG. 4; 55/68, 69; 62/12, 13, 24, 31, 32, 34, 40, 41, 42, 17, 20, 27, 28

[56] References Cited
U.S. PATENT DOCUMENTS
2,127,004 8/1938 Nelson ......................... 203/DIG. 4

Primary Examiner—Frank Sever
Attorney, Agent, or Firm—Richard P. Crowley

[57] ABSTRACT

A method for the distillative separation of a feed stream containing light hydrocarbons and acid gas components in a distillative column into an enriched overhead product, such as a carbondioxide fraction, and an enriched bottom product of $C_2+$ and hydrogen sulfide, the method which comprises: introducing a liquid alkane additive into the column, to provide a relatively uniform, constant temperature zone in the column above the point of feed inlet of the feed stream; extracting heat from the upper portion of the low-temperature zone; and introducing heat into the lower portion of the temperature zone approximately at or above the feed inlet of the feed stream, to reduce the energy requirement of the distillation.

24 Claims, 1 Drawing Figure

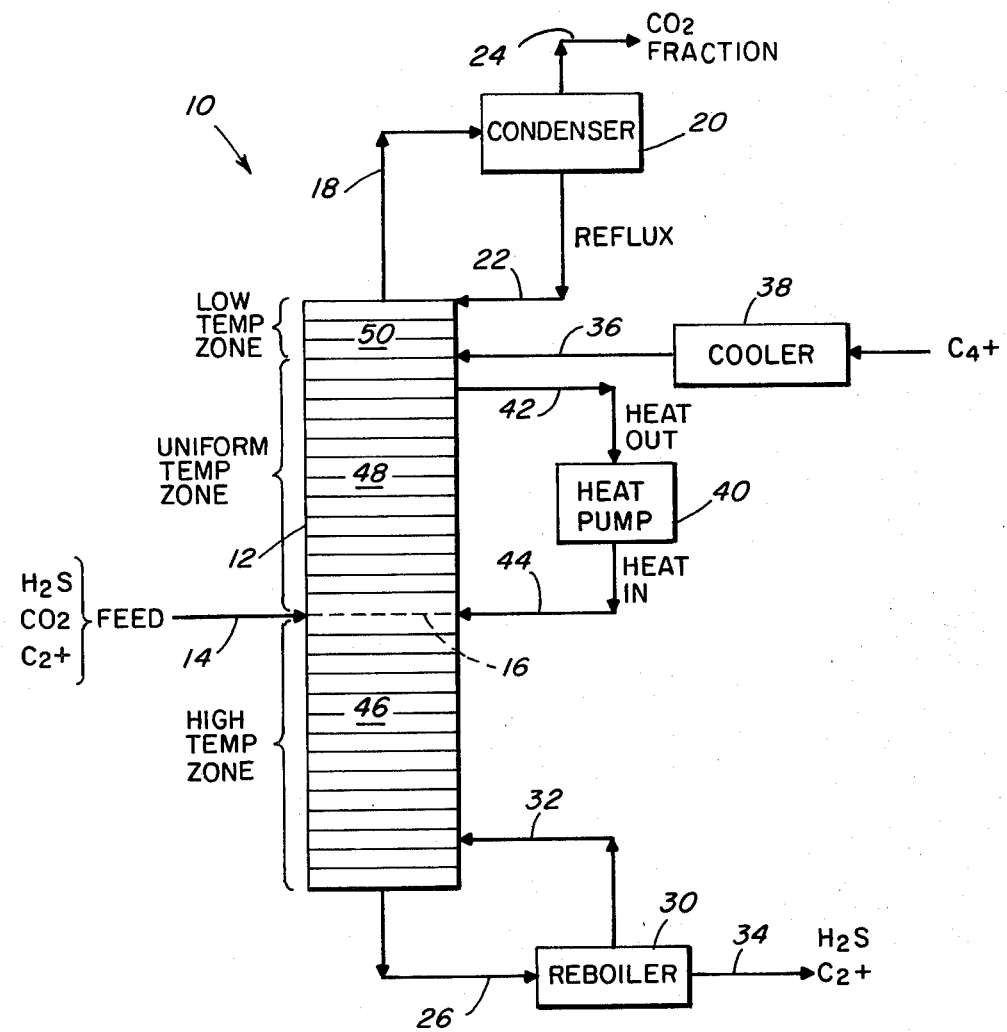

ENERGY-SAVING DISTILLATIVE SEPARATION USING LOW-TEMPERATURE HEAT INPUT

BACKGROUND OF THE INVENTION

It is often desirable to separate by distillative techniques a gas feed stream, such as one derived from natural gas or from petroleum or refinery operations, into one or more component fractions, either to recover a particular fraction or to remove an undesirable fraction from the gas stream. Typically, such distillation techniques involve introducing a gaseous, liquid or mixed-phase feed stream into one or more distillative columns containing vapor-liquid-contacting devices, such as trays, packing devices or combinations thereof, with the distillation temperature and pressure remaining at desirable conditions. An overhead product stream is removed, containing the lighter fractions, and a portion of the stream is at least partially condensed in a condenser and is recycled as a reflux stream, while a bottom product stream is removed, containing heavier components, and at least a portion of the stream, typically heated in a reboiler and recycled for use in the bottom of the column. The overhead product stream and the bottom product stream may be recovered and used or, if desired, sent for further separating or processing.

It has been found desirable also to introduce an additive agent particularly into the upper portion of the distillation column, in order to alter the distillation conditions, so as to enhance the recovery of the overhead or bottom products. For example, in U.S. patent application Ser. No. 94,226, filed Nov. 14, 1979 (now U.S. Pat. No. 4,318,723, issued Mar. 9, 1982), it was discovered that the use of a liquid additive agent in the cryogenic distillation separation of methane from a gas feed stream containing acid gas components was particularly effective for separating methane from high carbon-dioxide-content feed in a single distillative column, without the formation of carbon-dioxide solids. A liquid additive agent may comprise, for example, $C_3$-$C_6$ alkanes or mixtures thereof, sulfur dioxide or sulfur trioxide, and particularly butane-plus, as effective liquid additive agents to be introduced into the distillative column. The introduction of the liquid additive agent in the upper portion of the column and into the upper portion of the solids potential zone provided for the recovery of an overhead product stream of methane, and the removal of a bottom product stream containing carbon-dioxide methane and higher hydrocarbons and, optionally, hydrogen sulfide.

It also has been found that the use of additive agents may be employed usefully in the separation of acid gases, such as carbon dioxide, from ethane or from higher hydrocarbons in distillation processes, where normally the carbon dioxide and the ethane would form an azeotrope which would make distillation recovery of high fractions of the carbon dioxide difficult. For example, U.S. Pat. No. 4,350,511, issued Sept. 21, 1982, is directed to a method of separating carbon dioxide from a gas-stream mixture containing carbon dioxide and ethane, and wherein the distillative column is operated under conditions of pressure, temperature and composition to produce an enriched carbon-dioxide overhead product stream and an enriched ethane bottom stream. In the method, a liquid additive agent is introduced into the upper portion of the distillative column and in an amount sufficient to provide for a relative volatility of greater than 1 of the carbon dioxide to the ethane at or below the point of introduction of the liquid additive agent, thereby altering the possible formation of the azeotrope and permitting a carbon-dioxide-enriched overhead stream to be recovered.

Further, another use of a liquid additive agent, in order to increase the relative volatility of acid gas components, such as carbon dioxide and hydrogen sulfide, in a distillation technique is described in U.S. Pat. No. 4,293,322, issued Oct. 6, 1981. A distillative separation of carbon dioxide and hydrogen sulfide is shown to be improved by adding a liquid additive agent to the distillative column, which increases the relative volatility of the carbon dioxide to hydrogen sulfide, thereby increasing the separation efficiency, so that a carbon-dioxide fraction is removed in the overhead stream and a hydrogen-sulfide-enriched fraction and the liquid additive are removed with the bottom product stream.

In all of the foregoing patents, all hereby incorporated by reference, an additive agent is employed, particularly a liquid additive agent, and preferentially derived from one of the components in the feed stream, and is used to enhance separation efficiency. The liquid agent typically is miscible within the column and is at a point in the column below the column top. Also in all of the illustrations, the additive agent is usually removed, and the bottom product, or a portion thereof, is recycled back for use in the column or in other columns. If is, of course, desirable to improve such distillation techniques where additives are employed, to save energy and to increase the efficiency of the desired separation.

SUMMARY OF THE INVENTION

The invention concerns the distillative separation of feed streams into an overhead and a bottom stream, and wherein an additive agent is employed in the column, and wherein heat inputs into the column are effective for reducing the energy associated with the distillation. Particularly, the invention relates to the effective utilization of low-temperature heat inputs, to reduce the energy required for the distillative separation of carbon dioxide from hydrogen sulfide and carbon dioxide from ethane, plus higher hydrocarbons, in a cryogenic distillation method; for example, carried out at less than 40° F., employing liquid additive agents.

It has been discovered that the use of the additive agents in the distillative column, as described in the Background of the Invention, provides for a relatively uniform or constant temperature zone throughout the column, extending from the upper portion of the column from the point of introduction of the liquid additive agent to about the point where the feed stream is introduced into the column. The distillative column would have a number of theoretical stages described herein as trays, to provide effective gas/liquid contact in the distillation method. The upper trays of the distillative column, typically from about one to five trays, would be at a relatively low temperature; for example, less than 10° F., while the main body of the column downward approximately to the introduction of the feed stream; for example, twenty to fifty trays, has a relatively higher and constant temperature; for example, typically 10° F. to 30° F. or higher than in the upper low-temperature zone. The lower portion of the distillative column; for example, representing about the lower five to ten trays of the column, would operate at a relatively high temperature, typically over 60° F.; for example, 150° F. to 400° F. The overall temperature difference then within the column may vary, for example, from 300° F. to 400° F. or higher, with the relatively uniform, constant temperature shown occupying a major portion of the column between the upper portion of the column, wherein the liquid additive is introduced, and the lower end of the column or the intermediate portion of the column, wherein the feed stream is introduced. Of course, if the feed stream is introduced at multiple portions of the column or if the liquid additive is introduced into multiple points in the column, the relatively uniform constant temperature zone typically would extend to the lowest feed point and the highest additive point.

The employment of an additive agent, such as a liquid additive agent of the higher alkanes, also provides a uniform temperature profile within the distillative column during the distillation process. The relatively uniform constant temperature zone, within the intermediate portion of the column, tends to remain constant, because such zone is rich in the additive introduced. In the absence of the additive in the column, the relatively uniform temperature zone within the column would not be as uniform in temperature and would have greater temperature variations from the upper to the lower portions of the zone. For example, in the cryogenic distillation separation of carbon dioxide and hydrogen sulfide, the use of a normal butane liquid additive introduced into the upper portion of the column would provide for a relatively uniform, constant temperature zone of not greater than 10° F., while, without the use of the additive, the intermediate temperature zone in the column might vary as much as 30° F. to 40° F. or more.

It has been discovered that a significant energy savings may be accomplished and separation efficiency enhanced in those distillation processes, wherein an additive agent is added to provide a uniform temperature profile within the column, through the utilization of a low-temperature heat input to the bottom end of the relatively constant temperature zone of the column. The introduction of a heat input at the bottom end of the intermediate constant-temperature zone is effective for reducing the higher level heat inputs. The relatively uniform constant temperature zone in the column usually carries on down to the feed tray; that is, at the point or lowest point at which the feed stream is introduced into the column, and sometimes the constant-temperature zone may extend several trays below that feed tray, depending on the particular process, pressure, temperature and composition.

Therefore, the invention comprises utilizing a heat pump or its equivalent, which operates advantageously over a small temperature difference, or alternatively heat inputs at subambient temperatures are helpful, to save high-temperature fuel. It is recognized, of course, that heat can be added to the feed-tray inlet point through the use of heat in the feed stream. However, in many cases, the feed stream is already at a relatively high temperature, so that the separate lower introduction of heat is attractive in order to save energy, particularly where the heat input is derived from the upper portion of a column, or preferably the same column. Further, if a distillation separation has a great deal of vapor and liquid in the column, there are restrictions in the amount of heat which can be placed in the feed stream.

The invention employs the use of heat input at approximately the feed tray or just immediately below the feed tray; that is, at the bottom end of the relatively uniform, constant temperature zone in the distillative column. It is unusual in distillation techniques to apply heat or side reboiler at the middle of a distillative column or anywhere near the point of feed stream introduction; that is, near the feed additive tray or trays. However, it has been found that the introduction at this location is preferred, because the temperature at or immediately below the feed tray is at the bottom end of the constant temperature zone of the disillative column. Of course, some heat might be utilized in one or more trays slightly above the feed tray. Thus, contrary to conventional distillation techniques, the present invention contemplates the addition of heat at or above the feed tray, to effect savings in energy.

In one preferred embodiment of the invention, the relatively small temperature difference between the top and the bottom of the relatively uniform temperature zone is employed, and heat is typically withdrawn from about the top of the constant temperature zone and all or substantially all, or even a portion, of the heat is reintroduced into the feed tray or trays approximately at or above the feed inlet of the column. Of course, it is recognized that the heat input and heat output need not be balanced, nor may the heat input come from the heat output, and, in fact, it is contemplated that the heat input normally would be integrated with the typical refrigeration systems employed in the distillative column, or within the distillation scheme as a whole. In one embodiment, a heat pump or a similar device is employed to remove heat from the top portion of the relatively uniform, constant temperature zone and to reintroduce that heat into the lower portion of the same or a different constant temperature zone at or near the feed tray.

The present invention is useful in any distillation technique or column, wherein an additive is introduced into the column, in order to provide for a relatively constant temperature zone occupying a substantial portion of the column through the use of the additive, and wherein the temperature difference between the top and bottom temperatures of the zone is not too large. The invention finds particular utility where the energy difference in the bottom and top portions of the column is important, and wherein the additive can be removed easily from the bottom stream of the column and separated from the bottom product stream, and wherein the additive introduced into the column provides for a relatively uniform temperature zone in the column.

It is recognized that the prior art employs heat pumps with distillative columns; for example, in butane splitters and in propane and propylene distillation techniques. However, in these operations, there is no heat input required or needed near the feed tray or into the bottom of a constant-temperature zone. The present invention provides a significant energy savings in those distillation techniques, such as those described in the Background of the Invention, wherein an additive is employed to maintain a relatively uniform, constant temperature zone of low-temperature difference, and wherein the invention provides for a heat pump to introduce and recycle the heat from the top to the bottom of the constant temperature zone.

The amount of heat to be introduced or to be withdrawn depends upon the particular process employed, but typically the amount of heat input into the bottom of the column may vary, for example, from 1 mm BTU/hr to 20 mm BTU/hr per 1000 mols per hour of feed. The introduction of heat input into or about the feed tray provides for a reduction in the bottom reboiler load. The heat input into the column may be obtained through the use of a heat pump which is integrated with the temperature levels of the column, and with a main refrigeration system employed for liquefying, for example, a medium-pressure propane vapor stream. The use of a heat pump is intended to operate, where there exists an overall temperature difference within the column, typically over 300° F. to 400° F., and where a column contains a relatively uniform constant temperature zone having a small temperature difference, so that a great deal of energy work may be done in a particularly narrow temperature range; for example, less than about 20° F., such as 10° F.

The invention will be described for the purpose of illustration only in connection with a particular and specific distillation separation of carbon dioxide from hydrogen sulfide; however, it is recognized and is within the scope of the invention that a person skilled in the art may make various changes, modifications and improvements in the illustrative example, all falling within the spirit and scope of the invention.

BRIEF DESCRIPTION OF THE DRAWING

The drawing is a schematic flow diagram illustrating a distillative apparatus for carrying out the invention described herein.

DESCRIPTION OF THE EMBODIMENTS

The drawing shows a schematic illustration 10 of the invention as employed in the separation of a feed stream comprising $H_2S$, $CO_2$ and $C_{2+}$ into an enriched carbon-dioxide fraction in an overhead product stream and a hydrogen-sulfide-enriched $C_{2+}$ fraction as a bottom product stream. The system 10 includes a distillative column 12 containing distillation trays and having a feed inlet line 14 for the introduction of the feed stream about and intermediate the column. Although only one feed point is shown, of course the feed stream may be introduced at a plurality of points through the column 12. The feed stream is introduced at or about a feed tray 16 within the column, and a $CO_2$-enriched fraction is withdrawn as an overhead stream 18 and is fractionally condensed in a condenser 20. The reflux portion is sent through line 22 to the top of the column 12, while an enriched carbon-dioxide fraction is withdrawn through line 24. The hydrogen sulfide-$C_{2+}$-enriched fraction is withdrawn as a bottom product stream through line 26 to a reboiler 30, and a reboiled portion is sent through line 32 to the bottom of the column 12, and a bottom product stream of $H_2S$ and $C_{2+}$ is withdrawn by line 34. A liquid additive agent, such as butane alone or, more typically, as a major part of a $C_3$-$C_6$ alkane stream, is introduced into the upper portion of the column 12 through line 36, after passing through a cooler 38. The introduction of the additive agent provides a relatively uniform, constant temperature zone extending from about the point of introduction 36 to about the feed tray 16, as shown generally as 48, with a relatively low-temperature zone 50 at the top of the column 12 and a relatively high-temperature zone 46 at the bottom of the column 12.

Heat is withdrawn from the upper portion of the relatively uniform temperature zone 48 through line 42 by a heat pump 40 and recycled through line 44, with the heat introduced at or approximately at or just above the feed tray 16, to provide for energy savings by reducing the duty of the condenser 20 and the reboiler 30. The heat is introduced through line 44 at a subambient temperature to save on high-temperature fuel. The distillative system shown is carried out as described in U.S. Pat. No. 4,293,322, hereby incorporated by reference, except for the results achieved in the extraction and introduction of heat through the use of the heat pump in the inventive scheme.

The advantages achieved through the employment of the present invention have been illustrated by the data results of two distillations simulated on a computer; that is, Simulated Run No. 1 of Table I and Simulated Run No. 2 of Table II, wherein Simulated Run No. 1 is representative of a separation of a carbon-dioxide-enriched fraction as an overhead product stream and a hydrogen-sulfide-enriched fraction as a bottom stream, as illustrated in the drawing and as shown more particularly in U.S. Pat. No. 4,293,322. Simulated Run No. 2 is illustrative of the system conditions, wherein heat was extracted at the upper portion of the defined temperature zone and the heat input introduced into the column at the feed tray of the bottom of the uniform temperature zone. The data were obtained using a plate-to-plate column calculation program, to simulate process conditions within a distillative column under desired operating conditions. The trays are shown as theoretically perfect contact stages in the column. The program employed was the process simulation program of Simulation Sciences, Inc. of Fullerton, Calif., Version 1080. The vapor-liquid equilibria and thermodynamic data were calculated based upon the Soave-Redlich-Kwong equation of state. The data are believed to be representative of actual data and are appropriate for illustrating and for substantiating the benefits and advantages of the invention.

| TRAY NO. | TEMP. DEG. F. | NET FLOWS, LB. MOLES/HR. | | | | HEAT (COOL)ER DUTIES MMBTU/HR |
|---|---|---|---|---|---|---|
| | | LIQUID | VAPOR | FEED | PRODUCT | |
| | | | SIMULATED RUN NO. 1 | | | |
| 1 | 4.5 | 5822 | | | 4819L | −54.6 |
| 2 | 8.5 | 5667 | 10641 | | | |
| 3 | 17.5 | 8600 | 10436 | 2000L | | |
| 4 | 17.1 | 8601 | 11418 | | | |
| 20 | 16.9 | 8600 | 11420 | | | |
| 39 | 18.0 | 7706 | 11387 | | 4249V | |
| 40 | 23.6 | 9726 | 6275 | | 2598L | |
| 42 | 66.9 | 8290 | 5310 | | | |
| 43 | 118.2 | 5281 | 4261 | | | 45.0 |
| 47 | 342.1 | | 4014 | | 4029L | 40.0 |
| | | | SIMULATED RUN NO. 2 | | | |
| 1 | 4.5 | 4138 | | | 4821L | −46.0 |
| 2 | 8.6 | 4011 | 8960 | | | |

-continued

| TRAY NO. | TEMP. DEG. F. | NET FLOWS, LB. MOLES/HR. | | FEED | PRODUCT | HEAT (COOL)ER DUTIES MMBTU/HR |
|---|---|---|---|---|---|---|
| | | LIQUID | VAPOR | | | |
| 3 | 16.9 | 8895 | 8832 | 2000L | | −10 |
| 4 | 16.8 | 8898 | 11717 | | | |
| 20 | 16.6 | 8897 | 11719 | | | |
| 39 | 20.1 | 8798 | 11608 | 4249V | | |
| 40 | 39.9 | 8047 | 6370 | 2598L | | 10.0 |
| 42 | 104.9 | 7511 | 3733 | | | |
| 43 | 228.4 | 5128 | 3484 | | | 45.0 |
| 47 | 342.4 | | 3142 | | 4026L | 31.4 |

As shown particularly in Simulated Run No. 1 of Table I; that is, without the advantages of the present invention, the relatively low-temperature zone, at the top of the column, comprises trays or theoretical stages, 100% efficiency, 1–2 having a temperature range of 4.5° to 8.5° F. or a temperature difference of 4° F., while the relatively uniform constant temperature zone extends from tray 3 to feed tray 41 having a temperature range of 17.3° F. to 23.5° F. or a temperature difference of 6.2° F. The lower portion of the column, from tray 42 to tray 47, has a relatively high temperature ranging from 66.9° F. to 342.1° F. or a temperature difference of 275.2° F., with the total difference between the feed trays 1 and 47 being 337.6° F.

As shown in Simulated Run No. 2 of Table II, wherein 10 mm BTU/hr were extracted from the proportion of the relatively uniform constant temperature zone at tray 3, and the same amount of heat reintroduced at feed tray 41, as described in the invention, in such a column, the extraction of the heat and the introduction of the heat are accomplished by a heat pump, or by separate and equivalent devices or integrated with the total refrigeration system of the process. Simulated Run No. 2, with relatively low-temperature zone trays 1 and 2, ranges from 4.5° F. to 8.6° F., a difference of 4.1° F., while the relatively uniform temperature zone has an increased temperature profile ranging from tray 3 at 16.2° F. to tray 42 of 50.7° F., for a temperature difference of 34.5° F. The high-temperature lower zone (trays 42–47) ranges from 104.9° F. to 342.4° F., with the temperature difference now of 237.5° F.

The data from the Simulated Run No. 2 illustrate that heat inputs at the heat tray level of the bottom end of the constant temperature zone are effective for reducing high-level inputs at the bottom of the zone. In this illustrative example, heat is removed at about 17° F. and is introduced into the column at about 40° F. As shown, the difference is the extraction of 10 mm BTU/hr on tray 3 and the input of 10 mm BTU/hr on tray 40. Feed is added at trays 40 and 41. The advantages of the input show that the overhead condenser duty is reduced by 8.5 mm BTU/hr in response to the heat extracted at tray 3, while the bottom reboiler duty was lowered 8.6 mm BTU/hr in response to the heat input added to tray 40. The lower and intermediate temperatures were raised, including that of the side reboiler on tray 43.

The temperature levels also could be integrated with the main propane refrigeration system, using, for example, 40° F. in the present simulated example for liquefying a medium-pressure propane vapor stream, or employing ambient temperatures of water or air in the practice of the invention. The present invention makes cryogenic distillation; for example, the separation of carbon dioxide from hydrogen sulfide and carbon dioxide from ethane, more economical, and also may be employed in other industrial extractions and distillations employing an additive, wherein there is a separation in a narrow range of temperatures, typically less than 10° F.

What is claimed is:

1. In a method for the distillation of a feed stream in a distillative column containing vapor-liquid contact devices into an enriched overhead product stream and an enriched bottom product stream, and which includes introducing an additive into the column, to provide a relatively uniform constant temperature zone in said column above the feed inlet of the feed stream, the zone characterized by being more uniform in temperature than the temperature zone in the absence of said additive, the improvement which comprises:
   (a) extracting heat from the upper portion of the uniform temperature zone; and
   (b) introducing heat into the lower portion of the uniform temperature zone, the heat introduced approximately at or above the feed inlet of the feed stream to said distillative column, to reduce the energy requirements of the distillation, the extracting and introducing of heat carried out by an indirect heat exchange system.

2. The method of claim 1 wherein the feed stream comprises methane, acid gas components, nitrogen and $C_2+$ alkanes.

3. The method of claim 1 wherein the feed stream comprises carbon dioxide and $C_2+$ alkanes, and wherein the enriched overhead product stream is enriched in carbon dioxide and wherein the enriched bottom product stream is enriched in $C_2+$ alkanes and the additive.

4. The method of claim 1 wherein the feed stream comprises a mixture of carbon dioxide, hydrogen sulfide and hydrocarbons, and wherein the enriched overhead product stream comprises a carbon-dioxide-enriched fraction and wherein the enriched bottom product stream comprises a hydrogen-sulfide-enriched fraction.

5. The method of claim 1 wherein the distillative column includes a plurality of trays or packing devices, or a combination thereof.

6. The method of claim 1 wherein the additive comprises a liquid $C_3-C_6$ alkane.

7. The method of claim 1 wherein the additive comprises a liquid butane.

8. The method of claim 1 wherein the relatively uniform constant temperature zone in said column has a temperature difference, from the top to the bottom of the zone, of approximately 20° F. or less.

9. The method of claim 1 wherein the temperature of the upper portion of the relatively uniform temperature zone ranges from about 10° F. to 30° F.

10. The method of claim 1 wherein the temperature of the bottom of the relatively uniform temperature zone ranges from about 15° F. to 35° F.

11. The method of claim 1 which includes providing a reboiler for reboiling of the enriched bottom product and recycling a portion of the reboiled enriched bottom product to the bottom of the distillative column, and employing a condenser to condense at least partially the enriched overhead product stream and to recycle a portion of the condensed overhead product stream to the top of said distillative column, and providing a cooler to cool the additive stream introduced into the column, and integrating the extraction of heat from the upper portion of the temperature zone and the introduction of heat into the lower portion of the temperature zone with the condenser or reboiler.

12. The method of claim 1 wherein said distillative column is maintained at a pressure of from about 200 to 600 psi.

13. The method of claim 1 wherein the temperature difference within the column is not greater than about 350° F.

14. The method of claim 1 which includes employing a heat pump to extract heat from the upper portion of the temperature zone and to introduce all or substantially all of the heat so extracted by the heat pump into the lower end of the uniform temperature zone.

15. The method of claim 1 which includes introducing the heat into the lower portion of the uniform temperature zone in an amount approximately equal to the heat extracted from the upper portion of the uniform temperature zone.

16. The method of claim 1 which includes introducing the heat into the lower portion of the uniform temperature zone at a point extending from about the feed inlet to a point of approximately five stages above the feed inlet.

17. The method of claim 1 which includes introducing from about 1 mm BTU/hr to 20 mm BTU/hr per 1000 mols per hour of feed to the lower portion of the distillative column.

18. The method of claim 1 wherein the said column has a relatively low temperature zone of less than about 10° F. above the constant temperature zone and a relatively high temperature zone of over about 60° F. below the constant temperature zone.

19. The method of claim 1 wherein the overall temperature difference within the column varies from about 300° F. to 400° F. and the uniform temperature zone occupying a major portion of the column.

20. The method of claim 1 where the uniform constant temperature zone comprises from about twenty to fifty trays.

21. In a method for the distillation of a feed stream containing carbon dioxide and $C_2+$ alkanes in a distillative column, containing a plurality of vapor-liquid contact devices therein, into an enriched carbon-dioxide overhead product stream and into an enriched $C_2+$ bottom product stream, and which includes introducing a liquid $C_3$-$C_6$ alkane additive into the distillative column above the feed inlet of the feed stream, to provide a relatively uniform constant temperature zone in the column, the upper and lower portions of the zone not varying in temperature greater than about 10° F., the improvement which comprises:
 (a) extracting heat from the upper portion of the uniform temperature zone; and
 (b) introducing substantially all of the heat so extracted into the lower portion of the uniform temperature zone, the heat introduced approximately at or above the feed inlet of the feed stream to said column, to reduce the energy requirement of the distillation, the extracting and introducing of heat carried out by an indirect heat exchange system.

22. The method of claim 21 which includes employing a heat pump to extract the heat from the upper portion and to introduce the heat into the lower portion of the temperature zone.

23. The method of claim 21 which includes extracting the heat from the upper portion of the temperature zone, to reduce the temperature of the upper portion of the temperature zone not greater than about 10° F., and introducing the heat into the lower portion of the temperature zone to increase the temperature not greater than 10° F.

24. The method of claim 21 wherein the feed stream includes hydrogen sulfide and the enriched bottom product stream is enriched in hydrogen sulfide and contains the liquid additive.

* * * * *